United States Patent [19]
Wolf et al.

[11] Patent Number: 5,206,510
[45] Date of Patent: Apr. 27, 1993

[54] SPECTROSCOPIC ANALYSIS PROCESS FOR PLASTIC MIXTURES

[75] Inventors: Udo Wolf; Hans Dohmen, both of Krefeld; Jürgen Diefendahl, Neukirchen-Vluyn, all of Fed. Rep. of Germany

[73] Assignee: Bayer Aktiengesellschaft, Leverkusen, Fed. Rep. of Germany

[21] Appl. No.: 788,645

[22] Filed: Nov. 6, 1991

[30] Foreign Application Priority Data

Nov. 14, 1990 [DE] Fed. Rep. of Germany ....... 4036201

[51] Int. Cl.$^5$ ............................................. G01N 21/35
[52] U.S. Cl. .................................... 250/339; 250/340; 250/341; 250/360.1
[58] Field of Search ............. 250/339, 340, 341, 360.1, 250/358.1; 356/244

[56] References Cited

U.S. PATENT DOCUMENTS 3,737,235 6/1973 Hawes ............................. 356/432 X

FOREIGN PATENT DOCUMENTS 0295486 5/1988 European Pat. Off. .
1249565 11/1964 Fed. Rep. of Germany .
3416594 5/1984 Fed. Rep. of Germany .

OTHER PUBLICATIONS

Kubik, 'Rotation of Micro Samples for Infrared Spectrophotometer Analysis', Western Electric Technical Digest No. 3, 1966, pp. 21-22.

Primary Examiner—Constantine Hannaher
Assistant Examiner—Edward J. Glick
Attorney, Agent, or Firm—Sprung, Horn, Kramer & Woods

[57] ABSTRACT

The invention relates to a process for the analysis of plastic mixtures by infrared transmission spectroscopy in which the spectra are run while the samples are rotated. This measure improves the accuracy and reproducibility of the spectra and, hence, the determination of individual components of the plastic mixture.

4 Claims, 3 Drawing Sheets

SPECTROSCOPIC ANALYSIS PROCESS FOR PLASTIC MIXTURES

This invention relates to a process for the analysis of a sample of plastic mixtures by determination of infrared transmission spectra.

BACKGROUND OF THE INVENTION

The production and processing of plastics is characterized by constantly increasing demands on the quality of individual products. To meet these quality requirements, it is necessary to keep precisely to predetermined specifications particularly in regard to the concentration of individual constituents in plastic mixtures. In the context of the invention, plastic mixtures may be inter alia copolymers, polymer blends or filler- or fiber-reinforced plastics. Another field of application of the invention is the determination of additive concentrations. The additives in question are, for example, mold release agents or plasticizers. The concentrations of mold release agents are typically less than 1%. Nevertheless, their exact percentage content by weight in the plastic mixture often has to be determined.

There are already various known spectroscopic processes for determining the composition of plastic mixtures. In one frequently used process, a solution of the plastic is initially prepared and a transmission spectrum of the solution is then run. On the basis of absorption bands which are characteristic of the components to be determined, the concentrations of those components can be determined after calibration using the Lambert-Beer law or more recent evaluation methods. However, this process is attended by the disadvantage that there are no known solvents for certain modern high-performance plastics, for example polyphenylene sulfide, at temperatures below 150° C.

In addition, U.S. Pat. No. 4,717,827 describes a process in which the transmission measurement of the plastic to be analyzed is carried out on a molten sample. However, this process is suitable above all for the on-line production control of a product, but less suitable for the measurement of a number of different samples in a short time because cleaning and refilling of the measuring cell are relatively complicated. The most advantageous method of analyzing a number of different samples is to determine the transmission spectra of pressed films of the plastic mixtures to be analyzed. Pressed films are obtained in known manner by the compression-molding of a plastic mixture at a compression mold temperature above the melting temperature of the mixture to be analyzed. Their thickness is typically between 1 and 500 m. In addition, test specimens produced by injection molding with typical wall thicknesses of 0.1 to 100 mm may also be used for spectroscopic measurements. Since both pressed films or injection moldings and also the analysis beam of commercially available spectrometers often show an anisotropies or inhomogeneities, the spectra of these plastic films are subject to considerable variations which have a correspondingly adverse effect on the accuracy of the concentration measurement of individual components in the plastic mixture.

The problem addressed by the present invention was to provide a process for the analysis of plastic mixtures with increased accuracy by transmission spectroscopy using solid samples.

SUMMARY OF THE INVENTION

The present invention relates to method for the analysis of a plastic foil or film sample by determination of infrared transmission spectra in a Fourier transform spectrometer wherein the method comprises obtaining a plurality of distinct spectra while the specimen is rotated at an angular velocity so that the period of rotation is greater than the measuring time required to determine a single transmission spectrum and calculating the percentage contents of individual constituents in the specimen by averaging the data in the plurality of spectra.

According to the invention, the solution to this problem is characterized in that the spectra are determined while the samples are rotated and contents by weight of individual constituents of the plastic mixture are determined from the spectra by methods known per se.

The rotation of samples during the running of infrared transmission spectra is known per se and, hitherto, has mainly been used in the determination of molecular preferential orientations in polymer samples. In the development of the new process, it was found that rotation of the sample during running of the transmission spectra distinctly improves the quality of the concentration measurement. This applies irrespective of the time at which a mean value is determined from the plurality of measurements. Normally, an average spectrum is first determined from the plurality of spectra and is used to measure the concentration of the component to be determined by the methods described above. However, the concentration may also be initially determined from the individual spectra. The values thus obtained are then used to calculate the mean value. Both averaging techniques are well known, particularly in the field of Fourier transform infrared spectroscopy.

One particularly preferred variant of the new process is characterized in that the angular speed of the rotation is adjusted in such a way that the duration of the rotation is greater than the measuring time required to determine one of the transmission spectra.

The angular velocity of the rotation of the sample about the optical axis of the spectrometer is an important parameter in the application of the process and, in conjunction with predetermined parameters (available measuring time, required accuracy of measurement), is used to optimize the process. An excessively slow angular velocity increases the time required to carry out the new process. If the angular velocity is too high, more particularly above 1,000 Hz, considerable effort is required to shield the Fourier spectrometer against the effects of the mechanical movement. Angular velocities of 1 to 3 Hz have proved to be effective.

In another preferred variant of the process, the angular velocity of the rotation is continuously and/or discontinuously varied during determination of the spectra.

This process is of particular advantage when the individual transmission spectra of the polymer sample are to be determined at various defined angles $\alpha_1$. By synchronization of the spectrometer with the unit used to rotate the sample, it is possible for example to rotate the sample through $\delta\alpha = 10°$ before a spectrum is run and then to stop it again to run the spectrum. The 36 values thus obtained on completion of a full revolution can be used to carry out the averaging techniques mentioned above. The particular advantage of this process is that it minimizes the overall measuring time for a given plastic sample.

Another preferred embodiment of the process is characterized in that the transmission spectra are run in the wavelength range from 400 cm$^{-1}$ to 4,000 cm$^{-1}$. The characteristic bands of most molecules lie in this wavelength range.

BRIEF DESCRIPTION OF THE DRAWINGS

The process according to the invention is illustrated in the following with the aid of examples and a drawing. In the drawing.

Figure 1:
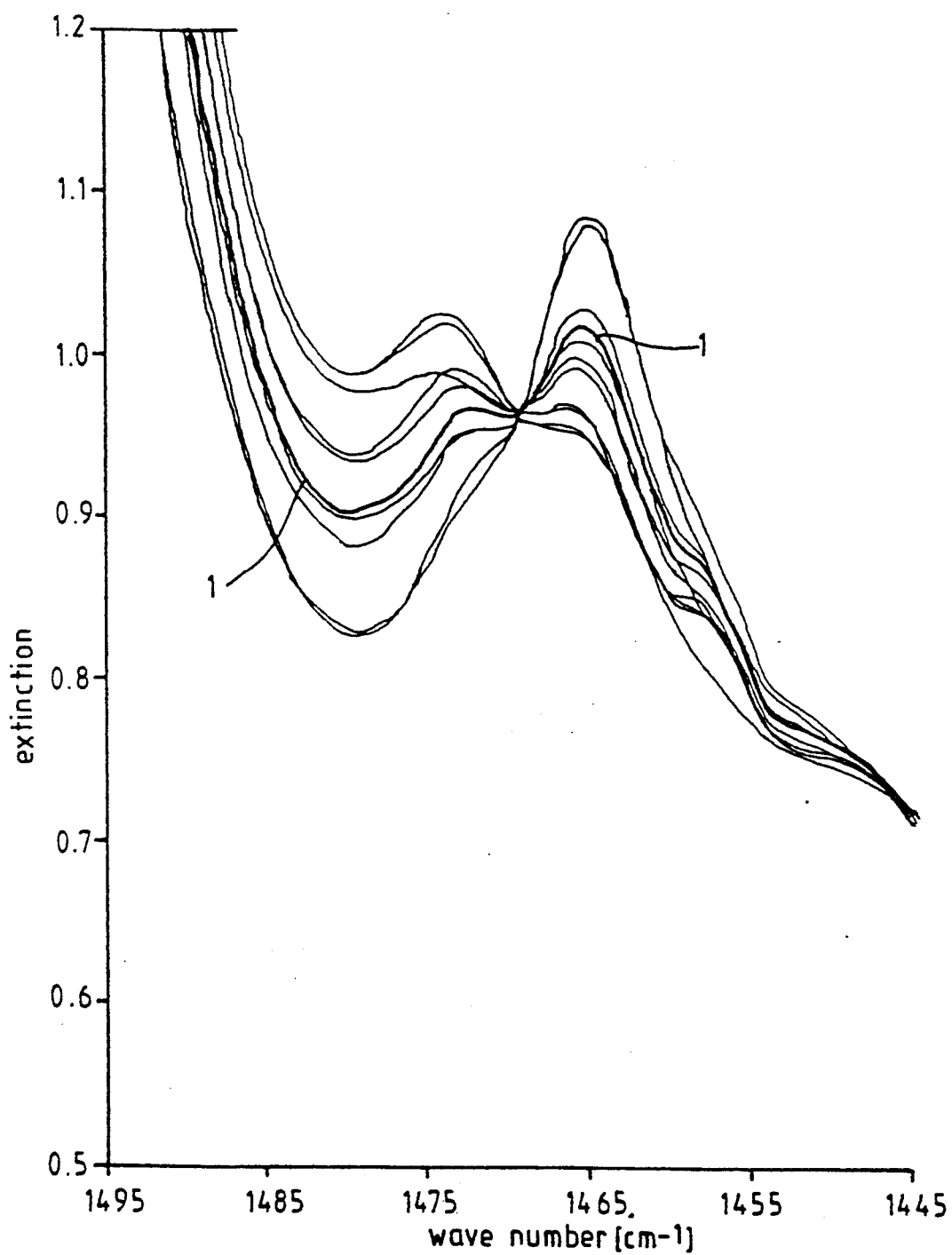
FIG. 1 shows part of the absorption spectrum of polycarbonate (extruded film).

The nine infrared transmission spectra of polycarbonate films from a single basic quantity shown in FIG. 1 were run with a commercially available Fourier transform spectrometer. The absorption maximum at 1,463 cm$^{-1}$ shows, for example, deviations of more than 10% between the absorption values of the individual samples at that wave number. These variations are of course carried over into any process for determining the concentration of individual components based on such a measurement of the infrared spectrum. Where the new process is applied, i.e. with rotation of the individual samples during running of the spectrum, the spectra of the individual samples are indistinguishable within the accuracy of measurement of the spectrometer (spectrum 1).

Figure 2:
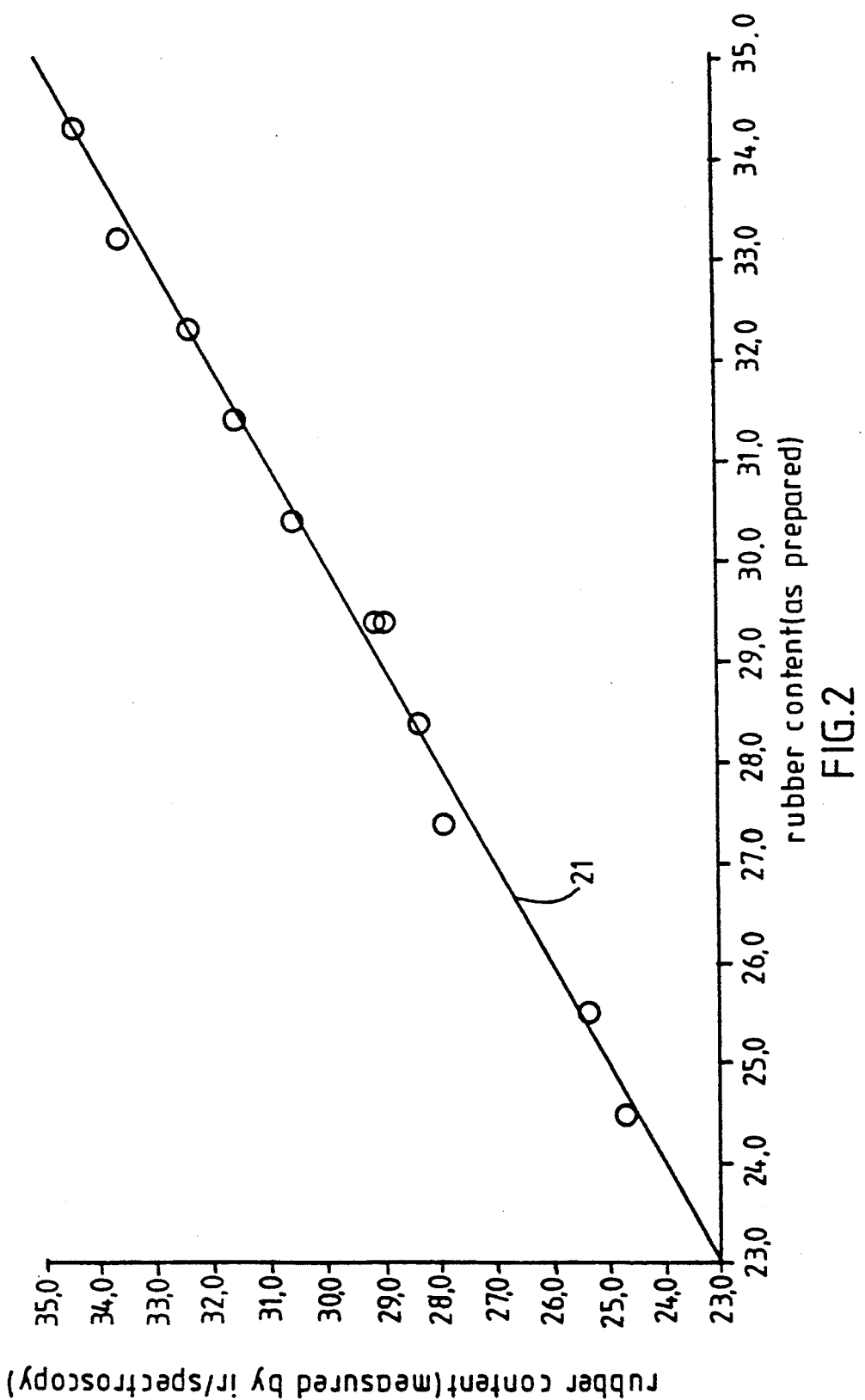
FIG. 2 is a comparison between the predetermined rubber content and the rubber content determined by the new process of several samples of a polyamide-based molding compound.

In addition, the new process was used, for example, to determine the percentage rubber content in impact-modified polyamide-6. In this concentration measurement, the problem was to determine a relatively high percentage content of a substance in the plastic mixture with high accuracy. Thus, the concentration of rubber in these impact-modified plastics is typically between 20 and 40%. For the measurement, 12 samples of known rubber content were analyzed by the new process. To this end, 20 to 50 μm thick hot-pressed films of the plastic mixture were placed in a rotatable sample holder and rotated at a frequency of 1.5 Hz. During this rotation, approximately 100 interferograms were accumulated by means of a standard Fourier transform infrared spectrometer (Nicolet 60 SX). The spectrum obtained after the Fourier transformation was evaluated by standard methods. To this end, the absorption band at 1,365 cm$^{-1}$ was used as the reference band for taking the layer thickness into account while the butadiene absorption band at 911 cm$^{-1}$ was used to determine the rubber concentration. FIG. 2 shows the measurement results in relation to the identity line 21. The standard deviation of the process is of the order of 0.05%.

Figure 3:
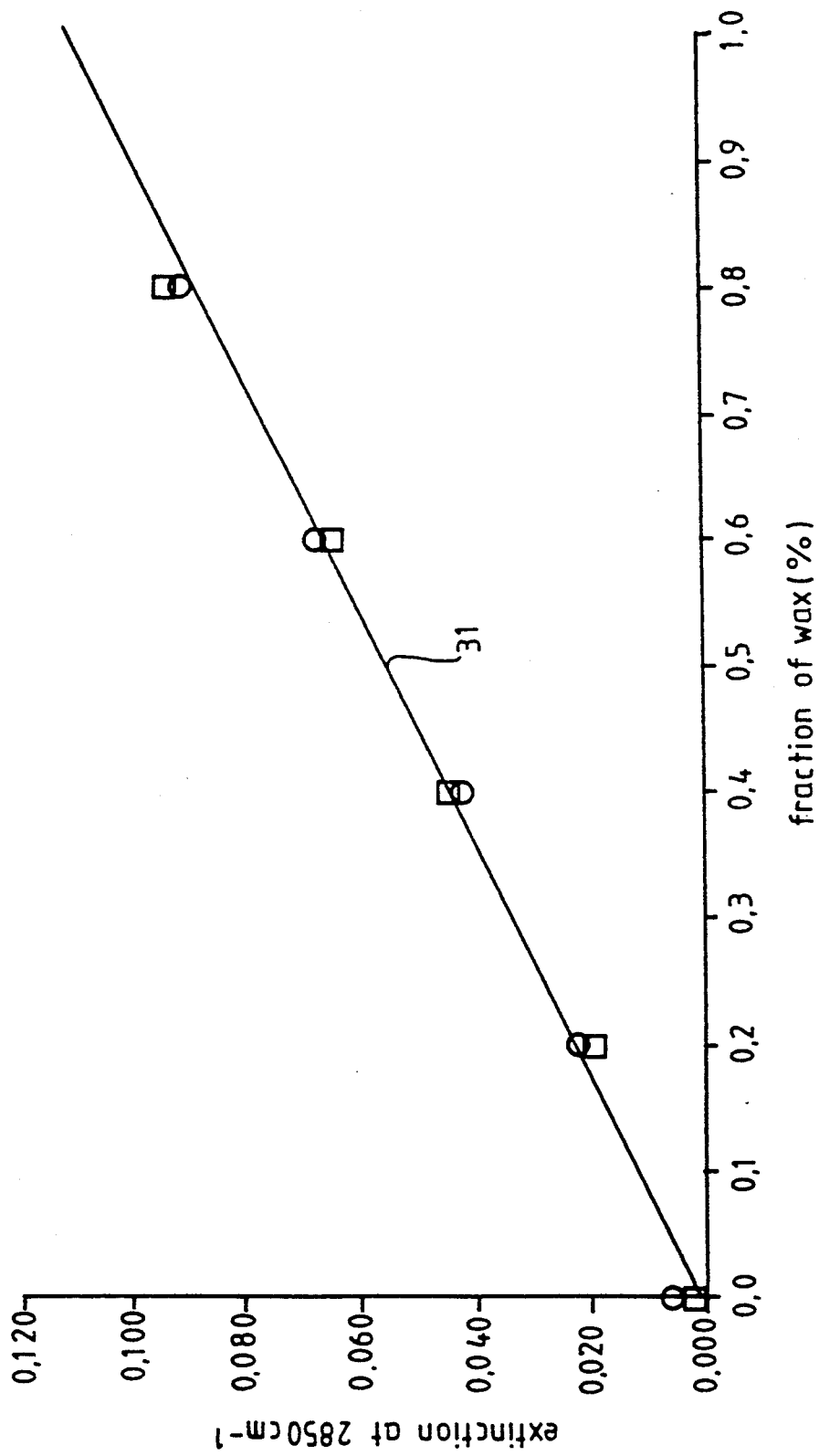
FIG. 3 is a comparison between predetermined and spectroscopically determined concentrations of a typical demolding wax in a polybutylene terephthalate.

In another example, the concentration of a demolding agent in polybutylene terephthalate (PBT) was determined. Since the concentration of such additives is relatively low (IR: 0.5%), based on the total quantity of plastic, the problem in this example was accurately to determine the concentration of a substance forming only a small part of the composition as a whole. The new process was carried out on samples having a defined content of demolding wax which were produced using a laboratory kneader. Extruded films having a thickness of 50 μm (measuring points characterized by squares) and 100 μm (measuring points characterized by circles) were produced to measure the IR transmission spectra. They were placed in a sample holder of which the frequency of rotation during the measurement was 2 Hz. The C-H stretching vibrational band at 2,850 cm$^{-1}$ was used as the absorption band of the demolding agent. FIG. 3 shows the calibration line 31 obtained on the basis of this measurement. Its accuracy is ±0.02%.

To improve the process, the spectrum of the pure basic substance (in this case PBT) stored in the spectrometer was subtracted from the spectra of the additive-containing sample in dependence upon the sample thickness and the differential spectrum thus formed was used as a basis for determining the concentration.

We claim:

1. A method for the analysis of an anisotropic plastic foil or film specimen in a rotatable sample holder by determination of infrared transmission spectra in a Fourier transform spectrometer wherein the method comprises
   a) obtaining a plurality of distinct spectra while the specimen is rotated at an angular velocity so that the period of rotation is greater than the time required to obtain a single transmission spectrum and
   b) calculating the percentage contents of individual constituents in the specimen by averaging the data in the plurality of spectra.

2. A method according to claim 1 wherein the angular velocity is 1 Hz to 3 Hz.

3. A method as claimed in claim 1, wherein the angular velocity of the rotation is continuously and/or discontinuously varied during the obtaining of the spectra.

4. A method as claimed in claim 1, wherein the transmission spectra are run in the wave number range from 400 cm$^{-1}$ to 4,000 cm$^{-1}$.

* * * * *